United States Patent

Bak et al.

[11] Patent Number: 6,066,788
[45] Date of Patent: *May 23, 2000

[54] GUZMANIA PLANT NAMED 'INTRO'

[75] Inventors: Gerardus J. Bak, Assendelft; Nicolaas D. Steur, Oude Niedorp; Elly Bak, Rijsenhout, all of Netherlands

[73] Assignee: Corn.Bak B.V., Assendelft, Netherlands

[*] Notice: This patent is subject to a terminal disclaimer.

[21] Appl. No.: 09/244,459

[22] Filed: Feb. 4, 1999

Related U.S. Application Data

[63] Continuation of application No. 08/794,592, Feb. 3, 1997, Pat. No. Plant 10,852.

[51] Int. Cl.7 ................ A01H 5/00; A01H 5/10; A01H 1/04
[52] U.S. Cl. ............ 800/323; 800/298; 800/260; Plt./334
[58] Field of Search .............. Plt./334; 800/298, 800/323, 260

[56] References Cited

U.S. PATENT DOCUMENTS

P.P. 10,852  4/1999  Bak et al. ................ Plt./88.8

*Primary Examiner*—Lynette R. F. Smith
*Assistant Examiner*—Melissa L. Kimball
*Attorney, Agent, or Firm*—Foley & Lardner

[57] ABSTRACT

A new cultivar of Guzmania named 'Intro' characterized by its bright relatively deep grayed-purple bracts, star-shaped inflorescence, relatively small and compact growth habit, superior floral bract production; arched, medium-green leaves, and by its long-lasting habit.

6 Claims, 3 Drawing Sheets

(3 of 3 Drawing Sheet(s) Filed in Color)

GUZMANIA PLANT NAMED 'INTRO'

This is a continuation-in-part application of U.S. patent application Ser. No. 08/794,592, filed Feb. 3, 1996, now U.S. Plant Pat. No. 10,852.

FIELD OF INVENTION

The present invention relates to a new and distinct cultivar of Guzmania that is an interspecific hybrid, hereinafter referred to by the cultivar name 'Intro'. The present invention relates to seed which are Guzmania cultivar 'Intro', plants and plant parts produced from these seed which have all the morphological and physiological characteristics of the Guzmania cultivar 'Intro', as well as to methods for producing these seed and plants.

BACKGROUND OF THE INVENTION

Guzmania are predominantly epiphytic plants with a few terrestrial species and are native to the tropics. For the most part species vary in diameter from 7 or 8 inches to 3 or 4 feet and have rosettes of glossy, smooth-edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short-lived.

Guzmania may be advantageously grown as pot plants for greenhouse or home use. Desirably the plants are shaded from direct sunlight and during the spring to autumn period the central vase-like part of the leaf rosette is desirably filled with water.

Guzmania are native to tropical America. Leaves of Guzmania are usually formed as basal rosettes which are stiff and entire and in several vertical ranks. Guzmania have terminal spikes or panicles which are often bracted with petals united in a tube about as long as the calyx. The ovary is superior and the seeds plumose.

Asexual propagation of Guzmania is frequently done through the use of tissue culture practices. Propagation can also be from offshoots produced by the plant which may then be rooted. The resulting plantlets are detached from the mother plant and may be potted up in a suitable growing mixture.

Methods for cultivation and crossing of Guzmania are well known. For a detailed discussion, reference is made to the following publications, which are specifically incorporated herein by reference: Benzing, David H., *THE BIOLOGY OF THE BROMELIADS*, Mad River Press, Inc., Eureka (1980); Zimmer, Karl, BROMELIEN, Verlag Paul Parey, Berlin (1986); and Rauh, Werner, BROMELIEN, Verlag Eugen Ulmer, Stuttgart (1981).

A Guzmania inbred is produced by selfing over several generations to produce a genetically homozygous plant selection. A hybrid culitvar is produced by crossing two genetically distinct inbred lines, collecting seed produced by the cross, and germinating seed so-produced to make hybrid plants. The hybrid seed and plants produced by this method are uniform with respect to their morphological and physiological characteristics.

A need exists for a greater variety of Guzmania cultivars with attractive ornamental features. Additionally, a need exists for additional Guzmania hybrid cultivars that can be easily propagated by seed.

SUMMARY OF THE INVENTION

These and other objectives have been achieved in accordance with the present invention which provides a new cultivar 'Intro' that is a product of a planned breeding program and was originated by the inventors from a cross made during such a program in Assendelft, The Netherlands, in 1990. The male or pollen parent was an inbred selection of *Guzmania lingulata minor* identified by Code No. 9013211. The female or seed parent was an inbred selection of *Guzmania lingulata lingulata* identified by Code No. 9013293. Both parents have a sufficient degree of homozygosity such that the progeny of the cross were, and continue to be, phenotypically uniform. The variety 'Intro' therefore can be produced by sexual reproduction by crossing 9013293×9013211 to produce a population of progeny plants, each of which has the combination of characteristics as herein disclosed for the new cultivar. Seeds produced by crossing 9013293×9013211 have been deposited with the American Type Culture Collection, 10801 University Boulevard, Manassas, Va. 20110-2209, and accorded Deposit Accession No. 203945.

The variety 'Intro' can also be produced by asexually reproducing progeny from the cross of 9013293×9013211 because the combination of characteristics as herein disclosed for the new cultivar 'Intro' are firmly fixed and are retained through successive generations of asexual reproduction.

OBJECTS OF THE INVENTION

This invention relates to seed which are Guzmania cultivar 'Intro', a representative sample having been deposited under ATCC Accession No. 203945.

This invention also relates to Guzmania plants, and parts thereof, having all the physiological and morphological characteristics of Guzmania cultivar 'Intro', representative seed which are said cultivar having been deposited under ATCC Accession No. 203945. This invention further relates to a pollen grain or seed produced by Guzmania plants having all the physiological and morphological characteristics of Guzmania cultivar 'Intro', represenative seed which are said cultivar having been deposited under ATCC Accession No. 203945. This invention also relates to seed produced on plants of the Guzmania cultivar 'Intro'.

This invention relates to a method of producing seed which are Guzmania cultivar 'Intro', representative samples having been deposited under ATCC Accession No. 203945, by crossing *Guzmania lingulata lingulata* selection 9013293 as the female parent with *Guzmania lingulata minor* selection 9013211 as the male parent and harvesting seed produced from said cross.

This invention also relates to a method of producing plants having all the physiological and morphological characteristics of the Guzmania cultivar 'Intro' comprising the steps of (a) crossing *Guzmania lingulata lingulata* selection 9013293 as the female parent with *Guzmania lingulata minor* selection 9013211 as the male parent; (b) harvesting seeds produced from said cross; and (c) producing plants from said harvested seeds.

BRIEF DESCRIPTION OF THE FIGURES

The file of this patent contains at least one drawing executed in color. Copies of this patent with color drawings will be provided by the Patent and Trademark Office upon request and payment of the necessary fee.

DETAILED DESCRIPTION

Figure 1:
FIG. 1 shows a perspective view of a typical plant of 'Intro', with the color of the primary bracts being fairly close to the true color, noted by color value below.
Figure 2:
FIG. 2 shows a top view showing the bracts and flowers of 'Intro' in more detail. The bract color shown in this photo is more red than the true bract colors specified below and shown in the photo in FIG. 1.
Figure 3:
FIG. 3 shows a close up view of the bracts and flowers of 'Intro'. Again, the bract color is not accurately depicted.

This invention is directed to a Guzmania plant having all the morphological and physiological characteristics of the cultivar 'Intro' produced from seeds which are the product of the cross of Guzmania lingulata lingulata selection 9013293 as the female parent with Guzmania lingulata minor selection 9013211 as the male parent. Both parents have a sufficient degree of homozygosity such that the progeny of the cross were, and continue to be, phenotypically uniform. The variety 'Intro' therefore can be produced by sexual reproduction by crossing 9013293×9013211 to produce a population of progeny plants each of which has the combination of characteristics as herein disclosed for the new cultivar.

The variety 'Intro' can also be produced by asexually reproducing progeny from the cross of 9013293×9013211 because the combination of characteristics as herein disclosed for the new cultivar 'Intro' are firmly fixed and are retained through successive generations of asexual reproduction. The selection comprising the new variety was chosen after commencement of flowering of the progeny in 1992 in Assendelft, The Netherlands. The selection was first asexually propagated through offshoots by or under the supervision of the inventors in Assendelft, with subsequent asexual reproduction being primarily by offshoots. Continuous asexual propagation has demonstrated that the combination of characteristics as herein disclosed for the new cultivar 'Intro', as observed in Assendelft, the Netherlands, are firmly fixed and are retained through successive generations of asexual reproduction.

'Intro' is particularly characterized by the following characteristics:

1. Solid compact growth habit in a funnel form rosette measuring approximately 22–23 cm in height above the pot when flowering. The cultivar is small both in height and overall diameter.
2. Numerous, relatively narrow leaves, each approximately 2.4 to 3.2 cm in width.
3. Superior floral bract production.
4. Star-shaped inflorescence.
5. Floral bracts are a bright relatively deep grayed-purple, which especially distinguishes the new cultivar from others, including the cultivar 'Ultra', disclosed in U.S. Plant Pat. No. 8,221.
6. Long-lasting habit.

'Intro' has not been tested under all available environmental conditions. The phenotype may vary with variations in environmental conditions such as temperature, light intensity, frequency of fertilization, composition of fertilizer, acetylene treatment, day length and humidity without, however, any change in the genotype of the new cultivar. For example, substantial differences in plant height and diameter, and the number of leaves, can result depending on the size of the plant at the time flowering is induced by acetylene treatment. Since treatment with acetylene to induce flowering disrupts normal watering and fertilization regimens, acetylene treatment of relatively smaller plants adversely affects the growth of the plant.

In comparison to the cultivar 'Ultra' referred to above, 'Intro' flowers approximately 3 weeks earlier after the same ethylene treatment. The leaves of 'Ultra' measure approximately 2.0 to 2.9 cm in width and therefore are slightly narrower than the leaves of 'Intro'. In addition, 'Intro' leaves arch from the base rather than only in the outer part of the leaf as in 'Ultra'. The leaves of 'Intro' are not striated while the leaves of 'Ultra' have distinct longitudinal grayed-purple striations. In addition, the floral bracts of 'Intro' are yellow-orange in the upper part with a white apex. The floral bracts of 'Ultra' are entirely grayed-purple having a color value with references to the Royal Horticultural Society (RHS) color chart 185A except for the apex of the inner floral bracts which are white. The sepals on 'Intro' are lanceolate compared to the obovate-lanceolate sepals of 'Ultra'. Further, the petals of 'Intro' are yellow-orange (17A RHS), compared to the much lighter yellow (9A RHS) petals of 'Ultra'.

The following traits have been repeatedly observed and in combination distinguish 'Intro' as a new and distinct cultivar. These observations, measurements and descriptions were taken for 'Intro' plants grown under the following greenhouse conditions in Assendelft, The Netherlands. The minimum day and night temperature was 20 and 18° C., respectively. The ventilation temperature was 24° C. and the maximum light intensity was 18000 Lux. Fertilizer concentration was 0.5 to 1 EC comprising N:P:K in the ratio of 1:0.25 to 0.5:2 to 3. In addition, 3% of the total amount of fertilizer was $MgSO_4$.

Frequency of fertilization varied depending on time of year and ranged from once per week to once per month. Fertilization was more frequent during the spring and summer months. Following fertilization, the plants were rinsed with sufficient clean water to remove residual fertilizer from the leaves. If fertilization frequency, or the concentration of fertilizer, is increased, 'Intro' leaves are darker in color, eventually resulting in burning of leaves and roots. If fertilization frequency, or the concentration of fertilizer, is decreased, 'Intro' leaves are lighter in color. If the ratio of N:K is increased above the value given above, 'Intro' leaves become darker in color, longer and more narrow. If the ratio of N:K is decreased below the value given above, 'Intro' leaves become lighter in color, shorter and broader. Fertilizer that contains too much P causes leaf tip burn and dark leaves while fertilizer that contains a suboptimal concentration of P produces 'Intro' plants with light leaf color.

With regard to induction of flowering, acetylene gas is allowed to bubble through 100 L of cool water for 30 min at a pressure of 0.5 bar. Whole plants are then sprayed with the acetylene solution making certain that the cup (vase) is filled. Spraying is done in the morning because the plants need light after this treatment and the plants are not watered again for at least two days. The plants are treated again, following this same protocol, one week later. The plants should not be fertilized for two to three weeks following treatment with acetylene but it is likely the flowers will not form and the bracts will remain green.

The description of the new cultivar 'Intro' reported herein is based on measurements and observations of plants grown from seed grown in two different groups under environmental conditions described above. The dates for sowing of seed, transplant, potting of plants, ethylene treatment and bloom for the two groups are shown in Table 1.

TABLE 1

| TREATMENT | DATE | |
|---|---|---|
| | Group 1 | Group 2 |
| Sow Seed | 10/23/90 | 11/24/93 |
| Transplant | 3/12/91 | 4/7/94 |
| Pot | 8/8/91 | 8/10/94 |
| Ethylene | 5/26/93 | 6/22/95 |
| Blooming | 7/31/92 | 8/25/95 |

I. PLANT
  Form: funnel form rosette
  Height: approximately 22–23 cm high when flowering
  Growth Habit: stemless
  Diameter: approximately 40 cm
  Variation: The foregoing dimensions can vary substantially depending on the timing of the ethylene treatment to induce flowering. When the plant is treated as a relatively small plant, the height and diameter of the plant will be smaller than if ethylene treatment was carried out on a much older and larger plant. This is well-known to those skilled in the art, with size of the plant being controlled by the grower based on the timing of the ethylene treatment.
II. FOLIAGE
  Size of leaf:
    Length: approximately 19–26 cm long.
    Width: approximately 2.4 to 3.2 cm.
  Shape of Leaf: linear—lanceolate
  Surface Texture: smooth
  Orientation: leaf blades arch continuously from base
  Variegation: none
  Color:
    Upperside, from 137A to 146A–B
    Underside, from 137C to 146C
      The color of the leaves can vary somewhat depending on growing conditions, e.g., the amount of fertilizer used, the amount of light, etc.
  Number: Many, with average number of leaves per plant at maturity being approximately 25. Number can vary considerably based on the size of the plant at the time of ethylene treatment.
III. BRACTS
  Length:
    Scape bracts: The lowest scape bracts are approximately 16 cm long. The scape bracts just below the primary bracts are approximately 9 cm long.
    Primary bracts: The lowest primary bracts are approximately 12 cm long. The bracts progress upwardly, they become shorter, with the top primary bracts being approximately 5 cm in length.
  Width: The scape bracts are approximately 3.0 to 3.5 cm wide, and the primary bracts are approximately 3.0 cm wide.
  Number: There are approximately 8 scape bracts and 14 primary bracts, which combine to make a full inflorescence.
  General shape: Recurved and ovate-lanceolate
  Texture: smooth
  Margin: entire
  Color: The upper surface of the primary bracts is 187B–C RHS. The upper part of the floral bracts are 17C RHS with a white apex. Occasionally, at the beginning of flowering, the primary bract color may contain a darker 187A RHS.
IV. INFLORESCENCE:
  Borne (stalks): erect
  Shape of inflorescence: singular (head)
  Size of inflorescence on stalk: The size of the inflorescence changes with maturity; at full flowering, inflorescence is approximately 8 cm in height and approximately 14 cm in diameter.
V. FLOWERS:
  General description: Contiguous, short pedicellate; pedicel 4–5 mm long; sepals membranaceous, slightly asymmetrical, lanceolate, obtuse and cucculate, nearly straight, approximately 2.3 cm long and 0.4 cm wide; petals fleshy.
  Individual Petals: (Disposed within the bracts)
    Length: approximately 5.5 cm
    Width: approximately 0.5 cm
    Quantity: approximately 30 flowers depending on the size of the plant
    Color: 17A RHS with a white top
  Time of blooming: A fully grown plant can bloom the entire year. Flowering starts approximately 9 weeks after treatment with acetylene.
  Duration of blooms: Each flower blooms one day and the total blooming period is about 6 weeks.
VI. REPRODUCTIVE ORGANS
  Ovaries: Superior: ellipsoid, about 9 mm long and contracted into the style; style elongate, many times as long as ovary.
  Stamens: 6 in number; included in cucculate apex of petals; filaments about 4 cm long, anthers dorsifixed, about 9 mm long.
VII. SEED CHARACTERISTICS
  Quantity: approximately 5,000 seeds divided over approximately 20 capsules, depending on the size of the plant.
  Texture: The seeds are plumose.
  Other: Since the plant is a hybrid, the seeds cannot be used for reproduction since characteristics cannot be passed through sexual propagation.

We claim:

1. Seed which are Guzmania cultivar 'Intro', a representative sample having been deposited under ATCC Accession No. 203945.

2. A Guzmania plant, or parts thereof, having all the physiological and morphological characteristics of Guzmania cultivar 'Intro', represenative seed which are said culitvar having been deposited under ATCC Accession No. 203945.

3. A pollen grain produced by said Guzmania plant of claim 2.

4. A seed produced by said Guzmania plant of claim 2.

5. A method of breeding comprising crossing Guzmania cultivar 'Intro', representative seed which are said cultivar having been deposited under ATCC Accession No 203945, with a second Guzmania plant and selecting progeny from said cross.

6. The method of claim 5, where said second Guzmania plant is 'Intro'.

* * * * *